United States Patent [19]

Hansche

[11] Patent Number: Plant 6,676

[45] Date of Patent: Mar. 14, 1989

[54] CHERRY TREE NAMED BROOKS

[75] Inventor: Paul E. Hansche, Davis, Calif.

[73] Assignee: The Regents of the University of California, Berkeley, Calif.

[21] Appl. No.: 107,135

[22] Filed: Oct. 9, 1987

[51] Int. Cl.[4] ..... A01H 5/03

[52] U.S. Cl. ..... Plt./37

[58] Field of Search ..... Plt./37

*Primary Examiner*—Robert E. Bagwill

*Attorney, Agent, or Firm*—Townsend and Townsend

[57] ABSTRACT

The new variety of Cherry Tree, named 'Brooks', produces early-maturing fruit of very high quality which is very large, symmetrical and uniform in size. The fruit ripens about one week after 'Early Burlat', and about one week prior to 'Bing'. The fruit is also characterized by having a fruit quality and firmness superior to 'Early Burlat' and sweet, well balanced rich flavor which is exceptional for early season maturity.

2 Drawing Sheets

DESCRIPTION

This invention relates to a new variety of cherry tree, named 'Brooks', which is the result from the cross of the cherry cultivars known as 'Ranier' and 'Early Burlat' made in 1969.

Selection 12-28, a seedling of the cross, was planted in February of 1970 and the fruit of the selection was first obsserved in 1976. Selection 12-28 was then planted at the University of California. Wolfskill Ranch at Winters, Calif., and in 1978 was asexually reproduced by bud grafting. Selection 12-28, named 'Brooks' has been tested in a number of locations and evaluated. The evaluation revealed the merit of this new variety of cherry tree and resulted in its selection as a promising cultivar.

The characteristics that distinguish 'Brooks' are its very high quality, early maturing fruit and outstanding ability to develop uniformly and exceptionally large size fruit. The fruit is quite symmetrical and ripens evenly about one week prior to the popular 'Bing' variety (unpatented). In comparison with 'Early Burlat', the fruit of 'Brooks' is larger, of higher quality and superior firmness. 'Brooks' has a flavor which is sweet, well-balanced and exceptional for early season maturity. The tree has demonstrated its ability to perform well in the warmer areas of the State of California.

Figure 1:
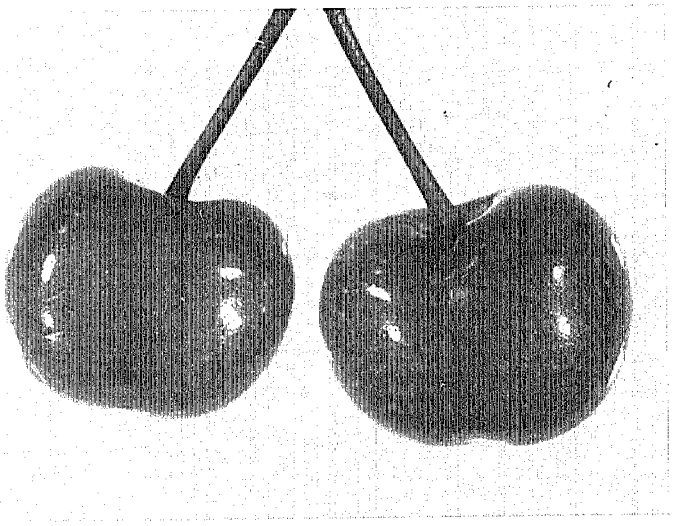
FIG. 1 illustrates the unique features of the fruit of the new variety.
Figure 2:
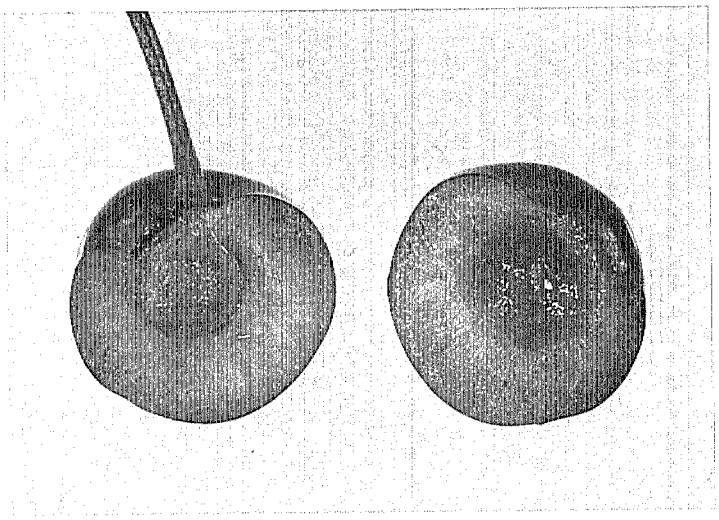
FIG. 2 illustrates the flesh color and fibers of the fruit when cut in transfer section.
Figure 3:
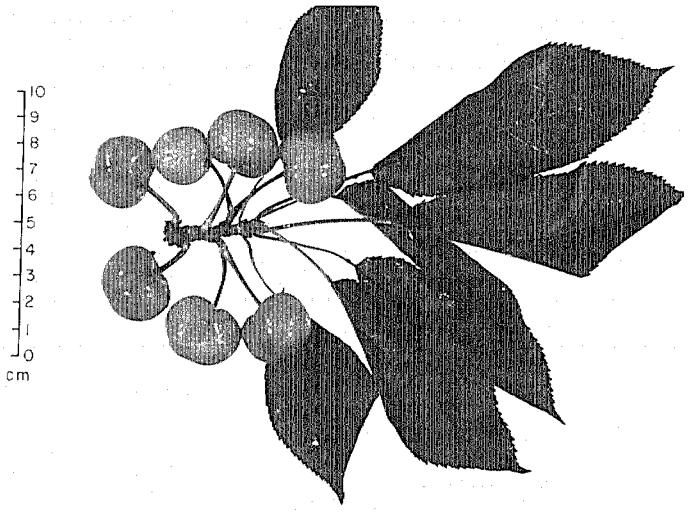
FIG. 3 illustrates a cluster of fruit and leaves typical of the new variety.
Figure 4:
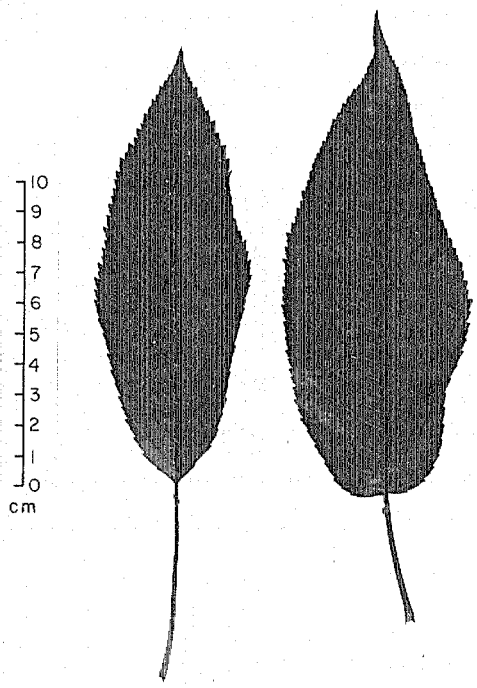
FIG. 4 illustrates mature leaves which are typical of the new variety.

The following specific description is of plant material obtained from a ten year old bearing cherry tree located in a test selection block at the University of California, Kearney Agricultural Center, Parlier, Calif. The fruit is described at firm maturity. Color definitions are from "Dictionary of Color" by Maerz and Paul, published in 1950.

SPECIFIC DESCRIPTION

Tree: Upright to upright spreading with form and density determined by pruning. Tree size slightly below average for species. Hardy for normal climatic conditions as found in the San Joaquin Valley of Central California. Very productive and regular bearer.

Trunk: Average in diameter, medium surface texture. Older bark brown-grey (7-E-10) to grey (7-A-9). Bark lenticels average in size and number.

Branches: Mature one year old branches medium in caliper and of smooth surface texture. Color of mature shoots grey-brown (7-E-10) with a moderate number of lenticels. Color of immature shoots, light green (19-G-3) with numerous raised light colored lenticels readily apparent over smooth surface.

Leaves: Measurements are from mature leaves attached at midpoint of actively growing upright shoots of current season's growth. Leaves large in size, average length 18.8 cm, average width 7.8 cm.

Form: Lanceolate with leaf tip acute to acuminate.

Color: Upper leaf surface, dark green (24-J-5). Lower leaf surface a light grey-green (22-D-4) with large mid vein yellow-green (18-H-4) in color and 1.5 mm in diameter in center.

Leaf petiole: Long average 4.5 cm in length. Average thickness 2.0 mm. Petiole color light green (18-H-5) at times some light reddish tinge along petiole groove.

Leaf glands: Large size. Form is most frequently oval to reniform but globose types can occur. Gland position is usually alternate with two to four glands located on rim of petiole groove 3 to 7 mm below basal leaf margin. Occasionally one or two more glands can occur along the basal edge of leaf margin. Gland color light green (18-I-4) and shiny with reddish center (4-C-10) when immature, darkening and becoming more red (5-H-11) with maturity.

Stipules: Large, usually two in number at base of petiole 1.5 to 1.8 cm in length. Color light green (18-G-5). Early deciduous.

Bloom Description

Bloom time: Early—between 'Early Burlat' and 'Bing'. Full bloom Mar. 18, 1987 at Parlier test site.

Flower size: Large, diameter 24–27 mm when fully open.

Bloom amount: Abundant, most commonly 3–5 flowers per cluster.

Flower bud scales: Dark grey-brown (8-C-9). Average size for species. Conic in form.

Petals: 17–20 mm in length; 12–14 mm in width. Form obovate. Short, wide truncate claw. Petals most commonly cupped inward and moderate undulate along margins. Petal color white (9-A-1).

Nectaries: Dull tan green (14-G-7) when young, lightening to grey-green (14-G-4) with age.

Anthers: Large, plump. Color yellow (10-J-2) both ventrally and dorsally. Occasionally there is an expression of an abnormality where pistils develop from the end of the filaments instead of anthers. Some individual flowers show a development of 5 to 6 of these abnormal pistils. Other commercial sweet cherry varieties also show this abnormality especially in warm interior valley locations.

Pollen: Abundant, color yellow (10-L-3).

Pedicel: Medium to slightly below average in length, 13–15 mm. Pedicel 1 to 1.5 mm in thickness, color pea-green (17-G-4).

Stamens: Moderately long, 11–16 mm when fully extended. Color white (9-A-1). Stamens: most commonly extended slightly beyond pistil at full floral maturity.

Pistil: 12–15 mm in length. Coloring very light-green 17-H-3.

FRUIT

Maturity: Date of first pick was May 10, 1987. Fruit hangs well on tree for at least 7 days to complete harvest.

Size: Uniform large size. Exceptional size for early season of maturity. Average cheek diameter 25.4 mm; average suture diameter 21.2 mm; average axial diameter 21.5 mm.

Form: Distinctive. Uniform and symmetrical. Form broadly oblate with a flattened and sometimes depressed apex. When viewed from the apical or basal end the fruit is quite uniformly oval.

Suture: A narrow but distinct dark red line (5-L-10); usually under 1.0 mm in width and darker than surrounding coloration. Suture not sunken or depressed over ventral surface. Occasionally suture slightly depressed within stem cavity.

Ventral surface: Very smooth, usually no lipping at all near mid-suture, and very slightly lipped over basal shoulder.

Stem cavity: Shoulders rounded with moderately broad cavity. Cavity round to very slightly oval in suture plane. Cavity width 11 to 13 mm, length 12–13 mm, 4–5 mm in depth.

Base: Rounded to slightly truncate. Base oblique to fruit axis, shorter on ventral surface side.

Apex: Truncate. Apex often moderately depressed. Pistil point apical and distinctive with moderate callousing of the stylar scar.

Stem: Variable: Medium to short in length, range of 24 to 35 mm. Color light green (21-G-6). Stem attachment strong—above average.

Skin: Firm, above average in thickness, tenacious to flesh. Susceptible to skin cracking caused by rain, especially in the week immediately preceding harvest.

Skin color: A dark red (4-L-11 over nearly 100 percent of fruit surface darkening with maturity to a red-burgundy (7-L-10). Some color streaking and mottling most commonly over basal shoulders. Mottling is lighter red than surrounding coloration. Numerous and conspicuous light colored dots and flecks over apical shoulders.

Flesh color: Variable, with rays and streaks of different shades of red and pink extending from skin to pit. Coloration varies from pink (2-F-9) to Rose (2-J-9). Fibers are numerous and very visible when fruit is cut in transverse section. Fiber color light varying from white to cream. Pit cavity darker than surrounding flesh. Cavity color rose (1-J-9). Stone nearly free, separates from flesh with relatively little clinging or fiber attachment. No air space in cavity. Juice dark pink to red, becoming darker with advancing maturity.

Flesh texture: Firm, crisp.

Ripening: Ripens evenly.

Flavor: Exceptional. Sweet, well balanced rich flavor well above average, especially for early season of maturity.

Aroma: Slight to lacking.

Overall eating quality: Exceptional.

Stone

Attachment: Nearly free, very few fibers cling to stone.

Size: Medium. Average length 10.5 mm, average width 9.5 mm, average thickness 7.5 mm.

Form: Roughly oval with small protruding wing along basal shoulder of ventral suture.

Base: Generally rounded but with low protruding wing along basal ventral shoulder.

Hilum: Small, oval. Slightly eroded on ventral end.

Apex: Rounded, almost no tip.

Sides: Symmetrical and almost always equal.

Stone surface: Lateral surfaces smooth with no pitting or grooves.

Ventral edge: Tight narrow suture subtended by two low ridges or wings converging basally and apically.

Dorsal edge: Very smooth with only a low tight narrow ridge from base to apex.

Stone color: (Dry) Straw colored (10-D-2).

Tendency to split: None observed.

Stone color: (Dry) Straw colored (10-D-2). Uniform.

Fruit use: Fresh market for local and long distance shipping.

Keeping quality: Good, based on limited testing.

Resistance to insects and diseases: No particular susceptibilities noted.

I claim:

1. I claim the new and distinct variety of Cherry Tree having the characteristics described and illustrated herein and the parts thereof.

* * * * *